(12) United States Patent
Anderson et al.

(10) Patent No.: US 10,953,235 B2
(45) Date of Patent: *Mar. 23, 2021

(54) SYSTEMS AND METHODS FOR TARGETED DEEP HYPERTHERMIA BY TIME-SHARED RF INDUCTIVE APPLICATORS

(71) Applicant: NEOTHERMA ONCOLOGY, INC., Wichita, KS (US)

(72) Inventors: Charles Eric Anderson, Lee's Summit, MO (US); Michael George Wandell, Seattle, WA (US); Randall Jones, Omaha, NE (US)

(73) Assignee: NEOTHERMA ONCOLOGY, INC., Wichita, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/318,948

(22) PCT Filed: Jul. 18, 2017

(86) PCT No.: PCT/US2017/042676
§ 371 (c)(1),
(2) Date: Jan. 18, 2019

(87) PCT Pub. No.: WO2018/017618
PCT Pub. Date: Jan. 25, 2018

(65) Prior Publication Data
US 2019/0299017 A1    Oct. 3, 2019

Related U.S. Application Data

(60) Provisional application No. 62/363,795, filed on Jul. 18, 2016.

(51) Int. Cl.
*A61B 18/10* (2006.01)
*A61N 1/40* (2006.01)
(Continued)

(52) U.S. Cl.
CPC .............. *A61N 1/403* (2013.01); *A61B 5/015* (2013.01); *A61B 5/055* (2013.01); *A61B 5/4836* (2013.01);
(Continued)

(58) Field of Classification Search
CPC ....... A61B 5/015; A61B 5/055; A61B 5/4836; A61N 1/403; A61N 5/025; G01R 33/34084; G01R 33/3415; G01R 33/4804
See application file for complete search history.

(56) References Cited

U.S. PATENT DOCUMENTS 5,186,181 A * 2/1993 Franconi .................. A61N 5/02
607/156
8,073,551 B2 6/2011 McCann
(Continued)

OTHER PUBLICATIONS

Extended Search Report for EP 17831723.6 dated Dec. 16, 2019.
(Continued)

*Primary Examiner* — Michael F Peffley
*Assistant Examiner* — Amanda L Zink
(74) *Attorney, Agent, or Firm* — Bryan Cave Leighton Paisner LLP

(57) ABSTRACT

The present disclosure provides, inter alia, a system and methods for targeted hyperthermia effective to differentially heat target organs. In certain embodiments, the system and/or method utilizes one or more pairs of inductive applicators coupled to the one or more RF generators and configured to deposit radio frequency radiation on a region of interest based on a set of configurable parameters.

32 Claims, 21 Drawing Sheets
(19 of 21 Drawing Sheet(s) Filed in Color)

(51) Int. Cl.
    *A61B 5/00*     (2006.01)
    *A61N 5/02*     (2006.01)
    *A61B 5/01*     (2006.01)
    *A61B 5/055*     (2006.01)
    *G01R 33/34*     (2006.01)
    *G01R 33/3415*     (2006.01)
    *G01R 33/48*     (2006.01)

(52) U.S. Cl.
    CPC ....... *A61N 5/025* (2013.01); *G01R 33/34084* (2013.01); *G01R 33/3415* (2013.01); *G01R 33/4804* (2013.01)

(56) References Cited

U.S. PATENT DOCUMENTS

| | | | |
|---|---|---|---|
| 9,333,369 B2 | 5/2016 | Ivkov et al. | |
| 10,354,838 B1* | 7/2019 | Mopidevi | H01J 37/3211 |
| 2007/0168001 A1 | 7/2007 | Xiang et al. | |
| 2008/0281318 A1 | 11/2008 | Herbette et al. | |
| 2010/0253348 A1* | 10/2010 | Wiggins | G01R 33/34046 324/318 |
| 2011/0118722 A1* | 5/2011 | Lischinsky | A61B 18/12 606/33 |
| 2012/0190912 A1* | 7/2012 | McKenna | A61B 5/0059 600/12 |
| 2015/0360057 A1 | 12/2015 | Balakin | |

OTHER PUBLICATIONS

International Search Report for PCT/US2017/042676 dated Sep. 28, 2017.
Written Opinion for PCT/US2017/042676 dated Sep. 28, 2017.

* cited by examiner

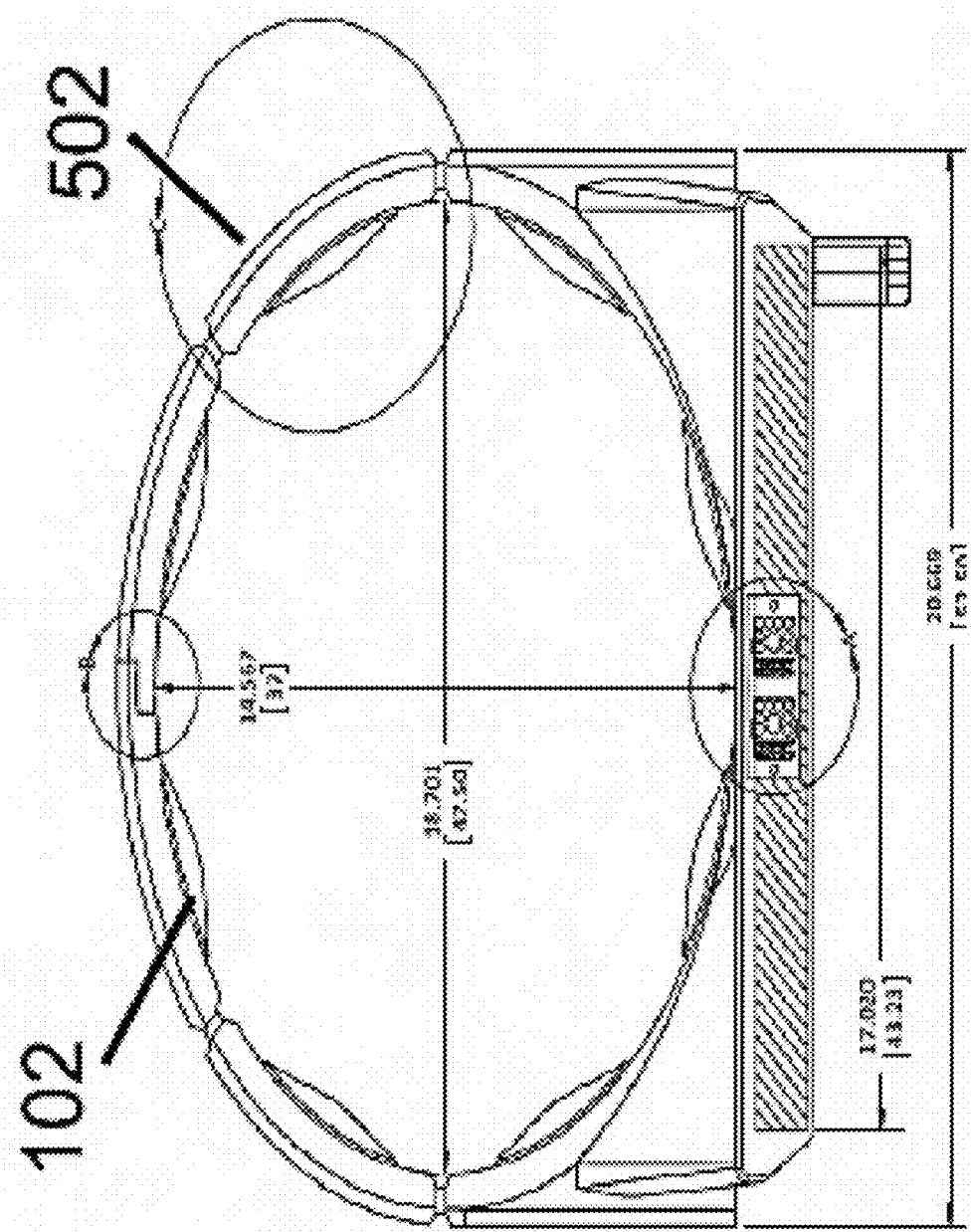

SYSTEMS AND METHODS FOR TARGETED DEEP HYPERTHERMIA BY TIME-SHARED RF INDUCTIVE APPLICATORS

CROSS-REFERENCE TO RELATED APPLICATIONS

The present application is the National Stage of International Application No. PCT/US2017/042676, filed on Jul. 18, 2017 which claims the benefit of U.S. Provisional Application No. 62/363,795, filed Jul. 18, 2016. The entire contents of the aforementioned applications are incorporated by reference as if recited in full herein.

FIELD OF THE INVENTION

The present invention relates to dynamically inducing targeted deep hyperthermia with increased selectivity and specificity due to timesharing of multiple Radio-Frequency (RF) inductive coils.

BACKGROUND

Targeted deep hyperthermia for applications such as cancer treatment, tumor ablation and treatment of other diseases relies on the exposure of the patient to RadioFrequency (RF) radiation of various frequencies, such as 13.56 MHZ, which allows for the heating of targeted cells (e.g., malignant/cancer cells) and their subsequent selective destruction alone or in combination with one or more anti-cancer therapies or therapy combinations such as radiation, and/or chemotherapy and/or immunotherapy. Generally, such techniques require the use of an applicator that delivers the RF radiation to the desired area of interest. For example, such applicators include a mechanical housing that envelops the necessary hardware components and typically is applied to the patient in order to cause heating of the desired area through the principles of capacitive coupling (e.g., displacement of current induced by an electric field), resistive heating, and radiative arrays. Furthermore, in order to ensure that there is no long term damage to surrounding healthy tissue these techniques require constant thermal monitoring as well as additional hardware (e.g., water filled bolus, air fans, etc.) that alleviate any issues relating to excessive heating such as, for example, dangerous heating of tissues outside the area containing a malignancy.

Targeted deep RF radiation-induced hyperthermia can provide therapeutic means for various cancer related therapies by selectively heating and thus destroying cancer cells while minimizing any possible effects to surrounding healthy tissue or it can be used in combination with existing anti-cancer treatments (e.g., radiation, chemotherapy, immunotherapy etc.) to increase their efficacy. Prior RF radiation-induced hyperthermia techniques, however, can be inefficient for deep targeting of cancer cells and solid tumors or provide inadequate safety margins without invasive temperature monitoring or extensive attempts and cooling the patient For example, techniques that rely on capacitive coupling require additional hardware to minimize heating of surrounding tissue as well as constant temperature monitoring through sensors (e.g., invasive thermometers) and/or diagnostic devices (e.g., Magnetic Resonance Imaging) that are time consuming and non-integrated in the therapeutic process and as a result can jeopardize the efficacy of the treatment.

SUMMARY

In some embodiments, systems and methods for targeted deep hyperthermia by time-shared RF inductive applicators are provided. Specifically, techniques for targeted deep hyperthermia allow for the destruction of malignant tissue (e.g., cancer cells) by selectively heating a region of interest without compromising surrounding healthy tissue by, for example, using one or more pairs of inductive coils that are controlled in a manner that allows for switching among the one or more pairs to provide a time-shared process. Such systems and methods allow for the optimal deposition of energy in the desired treatment area while avoiding the heating of non-malignant tissue and provide targeted and efficient treatment of cancer cells and tumors using real-time thermal monitoring and control of the radiation parameters by automatically providing feedback and adjustment of the configurable elements of the pairs of inductive applicators. As a result, such systems and methods provide both an independent treatment for malignant tissue destruction as well as an adjunct therapy in combination with chemotherapy, radiation and other anti-cancer treatments through multiple pathways, for example by increasing blood flow through heating, decreasing hypoxia (e.g., increasing oxygen levels in the region of interest), creating positive immune responses, inhibiting DNA repair and other cellular mechanisms.

In some embodiments, such pairs of inductive applicators utilize a hybrid drive that allows for the use of local radiated electric fields (e.g., E-fields) as well as the use of inductively coupled electric fields and magnetic fields (e.g., H-fields) that are generated by resonant magnetic field loops (e.g., coils). In some embodiments, such pairs of inductive coils are controlled in a time-shared manner whereby a selection is made to switch-on and/or switch-off the inductive applicators in order to provide targeted heating in the region of interest (e.g., malignant tissue) and/or minimize superficial heating outside the region of interest (e.g., healthy tissue). Furthermore, in some embodiments such applicators include resonant magnetic field loops of different sizes and/or material to allow for different targeted radiation depths.

In some embodiments, techniques for targeted deep RF-induced hyperthermia utilize Helmholtz type (in different planes and configuration) coils by placing opposing magnetic field loop pairs (e.g., coils) around a region of interest to create an inductively coupled magnetic field thus allowing for deep-seated electric field penetration. In some embodiments the one or more pairs of inductive applicators are not permanently connected and can be independently operated with any available coil in order to direct energy to a certain location not centered within the natural coil pairs. In some embodiments, the one or more pairs of inductive applicators can be chosen to be slightly off-axis. For example, such offaxis targeting can be achieved by varying the different pairs of inductive applicators and/or their respective sizes, providing temporal switching (e.g., time sharing), providing power (amplitude) modulation and mechanical displacement. In addition, in some embodiments, one or more of the pairs of inductive applicators are allowed to overlap by, for example, 90° or any other suitable value in order to increase the diameter of the inductive loop and thus the depth of heating.

In some embodiments, the one or more pairs of inductive applicators include one or more reflective shields in order to ensure uniformity of the induced electric filed (e.g., E-field) irrespective of the radiation location depth by modifying the electric and magnetic field deposition patterns. Specifically, such reflective shields can be included in flexible articulated links of the inductive applicators to ensure consistent contact with the patient, increase of patient's comfort and less tuning of the radiation parameters (e.g., power, frequency etc.).

In some embodiments, systems for targeted deep RF-induced hyperthermia are driven by a single RF generator and power divider that may be 0° or 180° phase separate. In some embodiments, two RF generators are used that may be 0° or 180° phase separate. In some embodiments, one or two RF generators may be used and the selection of their phase angle will be made by use of electronic switching, controlled similarly to the selection of inductive coils. For example, in such cases targeted hyperthermia is achieved by selecting a pair of inductive applicators using electronic switches and subsequently providing RF radiation using the either in phase or out of phase generators which change the SAR pattern in the target.

In addition, in some embodiments, systems for targeted deep RF-induced hyperthermia are automated with real-time magnetic resonance (MR) thermometry by, for example, providing integrated inductive MRI coils at the resonant frequencies of the supported MRI system. Specifically, such systems include MR integrated coils that provide real-time or near real time thermometry feedback to ensure for efficient heating of cancer tissue and minimize any possible side-effects and/or discomfort to the patient. In some embodiments, the inductive applicators and MR coils can be located in separate mechanical housings and/or in the same mechanical housing that can be overlapped in order to create different sizes that uniquely cater to the different patients. Furthermore, such integrated systems can include solid-state switches that are MR compatible to provide switching along the inductive applicators in order to minimize cable matching issues (e.g., dissipation of power) and/or include solid-state switches located in the magnet room in order to minimize the use of hardware equipment (e.g., cables) through operational panels (e.g., penetration panels).

In some embodiments, integrated MR inductive applicators include MR coils and hyperthermia inductive applicators (e.g., coils) that are made transparent to each other by geometric and/or tuned blocking circuitry to avoid interference and current leakage. In some embodiments, such integrated systems can deactivate one or more inductive applicators that are not in use during RF induced hyperthermia treatment. In addition, in some embodiments, real-time thermometry monitoring can be achieved by using and/or adding embedded thermal probes.

In some embodiments, systems for MR integrated, targeted deep RF-induced hyperthermia include software for automatically learning and adjusting heat deposition patterns using real-time MR feedback. For example, such software can include machine learning techniques (e.g., SVMs, neural networks etc.) and/or any other suitable learning algorithm. Specifically, a patient's individualized heat map can be monitored in realtime using the integrated system and a temporally adjusted plan of inductive applicator pairs and their respective power can be created for the remainder of the treatment. In some embodiments, an initial heat map may be obtained using population estimates and/or existing models and subsequently adjusted using the integrated system's real-time monitoring capabilities. In some embodiments, such individualized maps can be transmitted using one or more transceivers and/or servers to the manufacturer in order to provide data for treatment improvement.

According to some embodiments, the one or more pairs of inductive applicators further comprise at least six semi-planer inductive loops equally spaced circumferentially around the patient and configured to be temporally switched to provide targeted heating or minimize superficial heating outside the region of interest.

According to some embodiments, the system is effective to heat at least one of the patient's organs to a temperature that is at least 0.5° C. greater than the temperature of another of the patient's organs. In some embodiments, the system is effective to maintain a temperature differential of at least 0.5° C. between two or more of the patient's organs for at least 40 minutes.

According to some embodiments, at least one pair of inductive applicators is effective to differentially heat at least one organ in the patient relative to another organ. In some embodiments, at least one pair of inductive applicators is effective to differentially heat at least one internal organ relative to another internal organ of the patient. In some embodiments, the system is effective to differentially heat the patient's kidney relative to at least one other internal organ. In some embodiments, the system is effective to differentially heat the patient's pancreas relative to at least one other internal organ.

According to some embodiments, the system is effective to differentially maintain the temperature of the patient's kidney at least 0.5° C. above the temperature of at least one other internal organ.

According to some embodiments, the system is effective to differentially maintain the temperature of the patient's pancreas at least 0.5° C. above the temperature of at least one other internal organ.

According to some embodiments, the one or more RF generators are used and the selection of their phase angle is made by use of electronic switching.

DEFINITIONS

MR=magnetic resonance
MRI=magnetic resonance imaging
E-field=Electric Field
H-field=Magnetic Field
SNR=Signal-to-noise ratio
RF=radiofrequency
SAR=Specific Absorption Rate

BRIEF DESCRIPTIONS OF THE DRAWINGS

The patent or application file contains at least one drawing executed in color. Copies of this patent or patent application publication with color drawing(s) will be provided by the Office upon request and payment of the necessary fee.

FIG. 1A shows a magnetic field (H-field) plot of a cross sectional side view of the apparatus according to some embodiments of the invention (e.g. FIG. 4A, FIG. 6F). Inductive coils (not all depicted) are 22-24 cm loops, with 3 in the base and one in each section of the top. The plot goes from yellow (highest strength) to pink (middle strength) to blue (lowest strength), demonstrating the H-fields that the coils emit. The inner structure depicted is a molded homogenous structure with electrical properties representative of 85% human muscle and 15% fat.

Figure 1A:
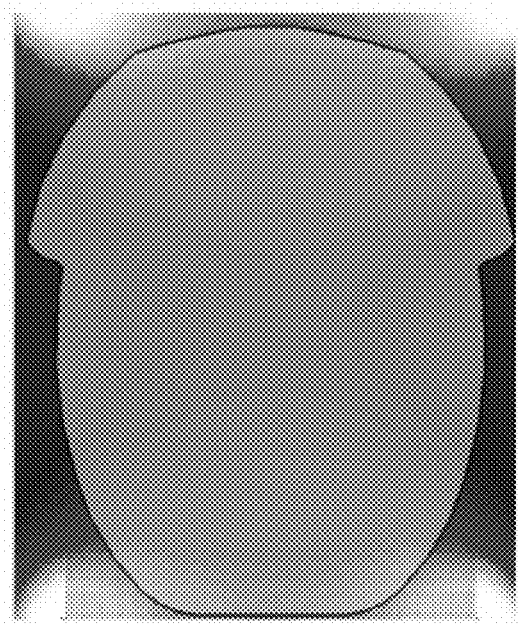
FIG. 1B shows a SAR plot of a time-averaged simulation of an 8 coil applicator where the coil pairs are shared in an equal time allotment and the resulting hot spot is centralized.
FIG. 1C shows a SAR plot of a time-averaged simulation of an 8 coil applicator system where the coil pairs are shared with non-symmetrical time allotments and the pairs themselves are selected as off-axis pairs, resulting in an off-center hot spot.
Figure 1B:
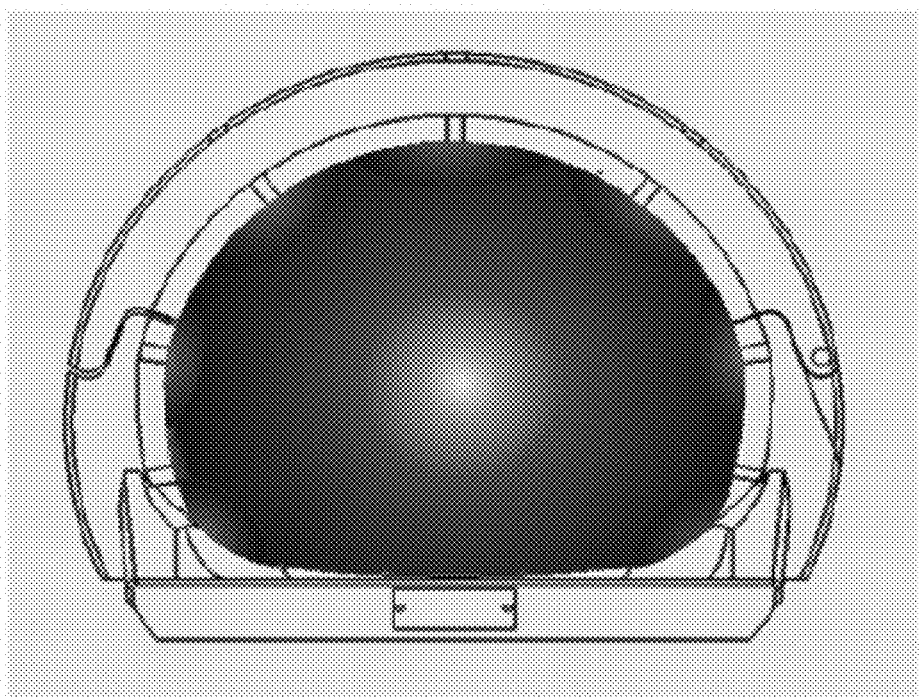
Figure 1C:
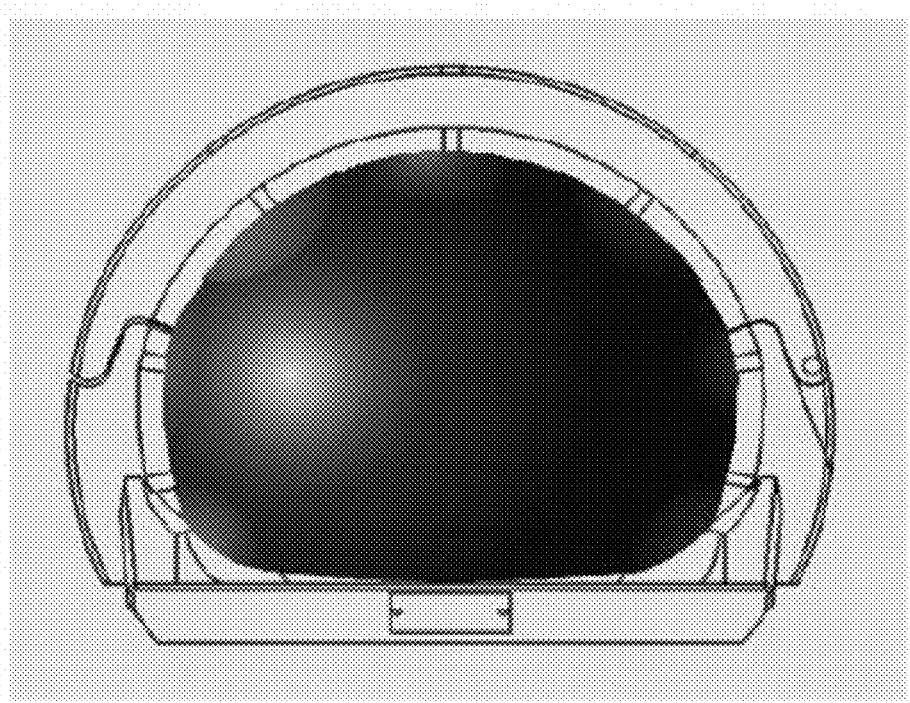
Figure 1D:
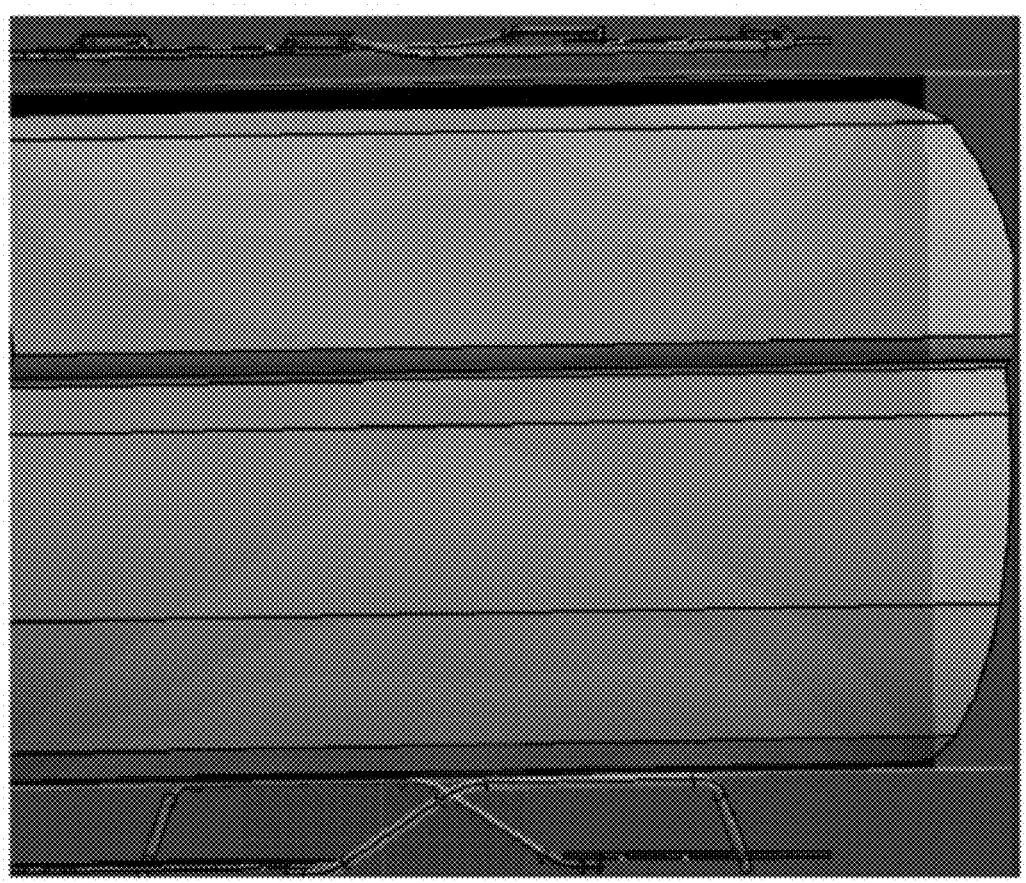
Figure 1:
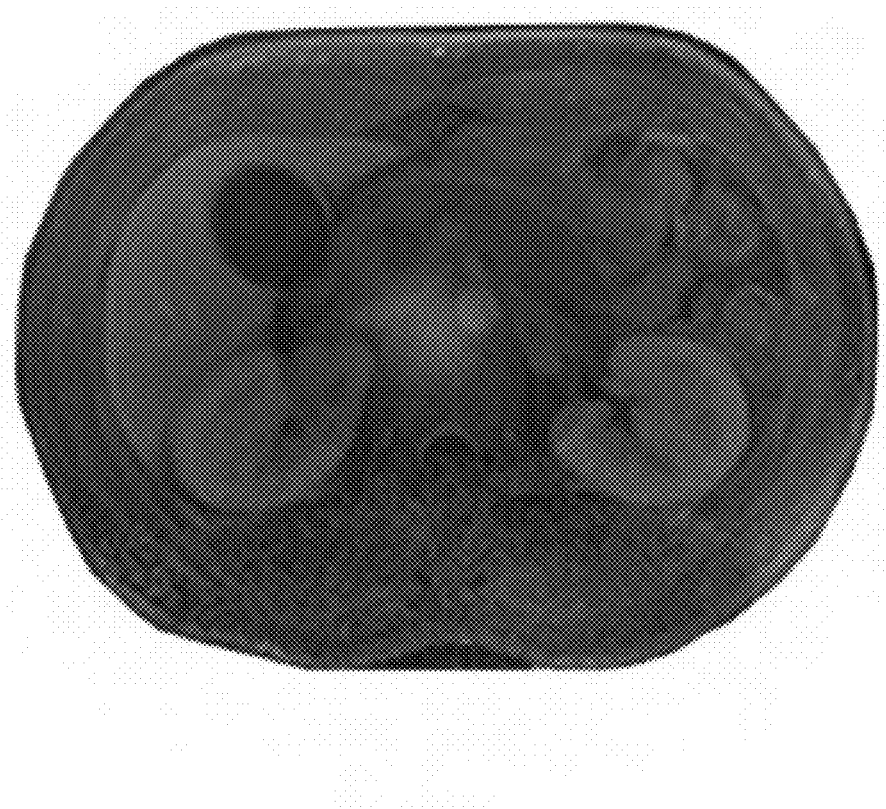

FIG. 1D shows a magnetic field (H-Field) plot of a cross sectional front view of the apparatus of FIG. 1A. Inductive coils (not depicted) are 22-24 cm loops, with 3 in the base and one in each section of the top. The plot goes from yellow (highest strength) to pink (middle strength) to blue (lowest strength), demonstrating the H-fields that the coils emit. The inner structure depicted is a molded homogenous structure with electrical properties representative of 85% human muscle and 15% fat.

FIG. 1E shows a MRI image of a human torso overlaid with a hypothetical rendition of a time-averaged heat map according to one possible embodiment of the invention.

Figure 2:
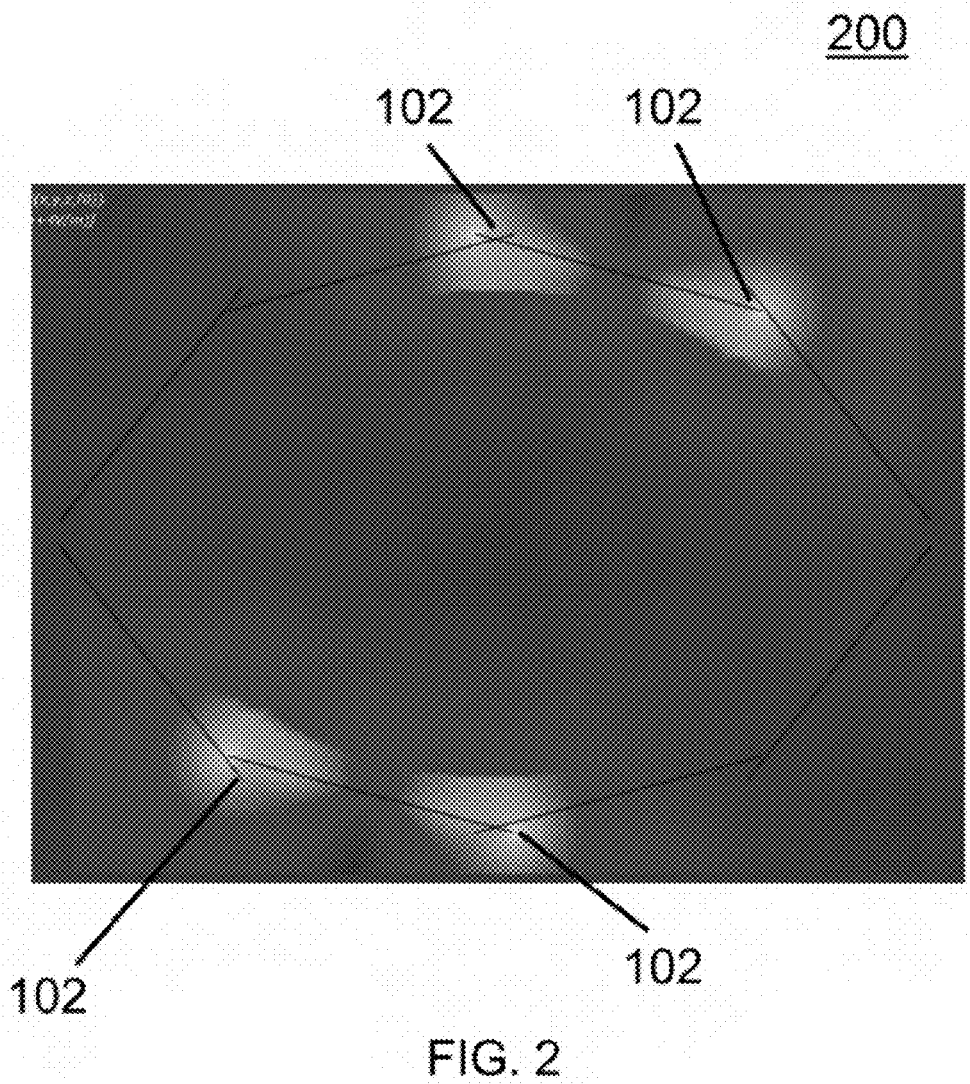

FIG. 2 is an example of resonated pairs of inductive applicators and a resulting E-field plot for targeted deep RF radiation-induced hyperthermia.

Figure 3:
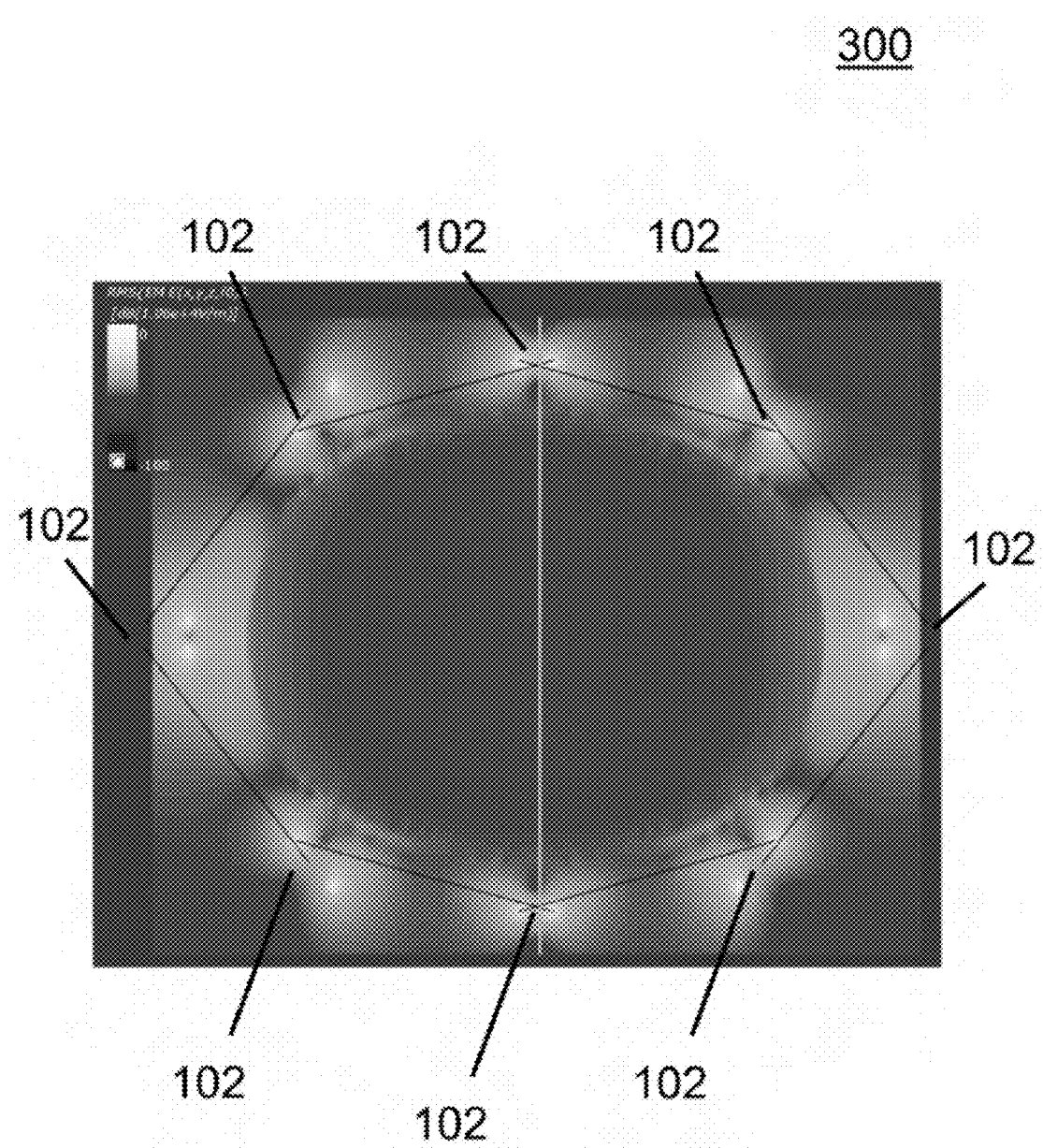

FIG. 3 is an example of a system in which all applicators are active at the same time, in which all electronic switches are short. The resulting heat map produces broad general RF radiation induced hyperthermia.

Figure 4A:
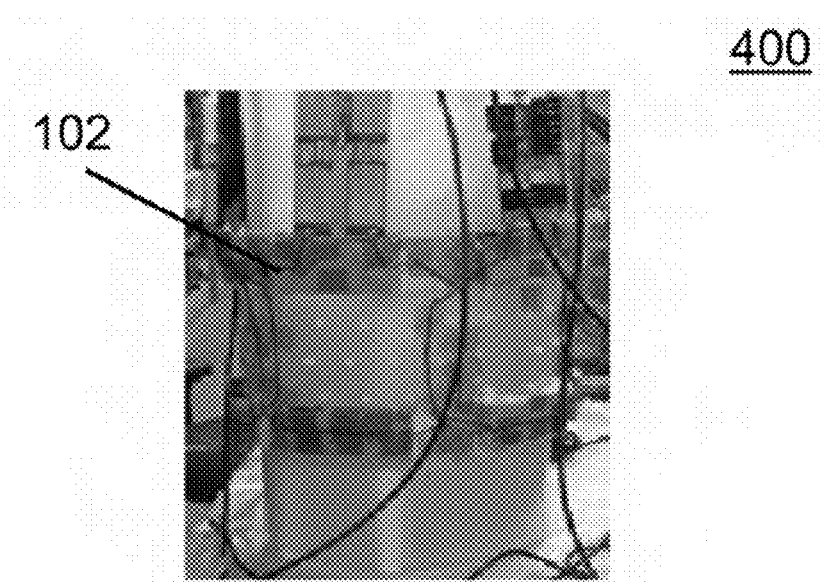

FIG. 4A is an illustration of the time-shared inductive applicator pairs for targeted deep RF radiation-induced hyperthermia.

Figure 4B:
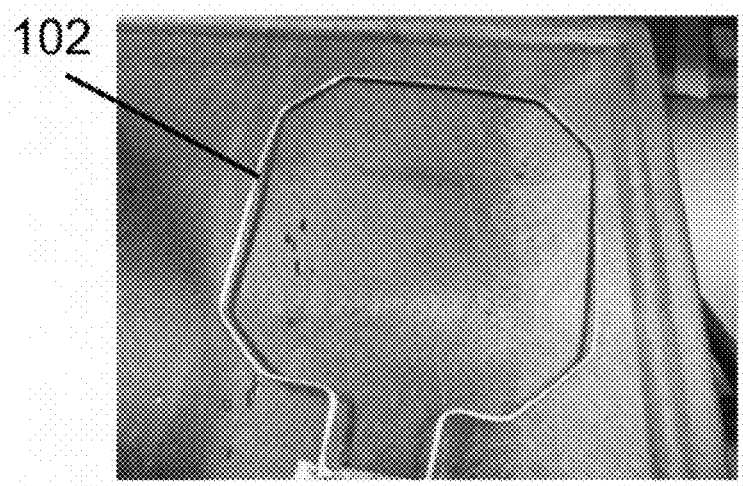

FIG. 4B is an example of a single inductive applicator for targeted deep RF radiation-induced hyperthermia.

Figure 4C:
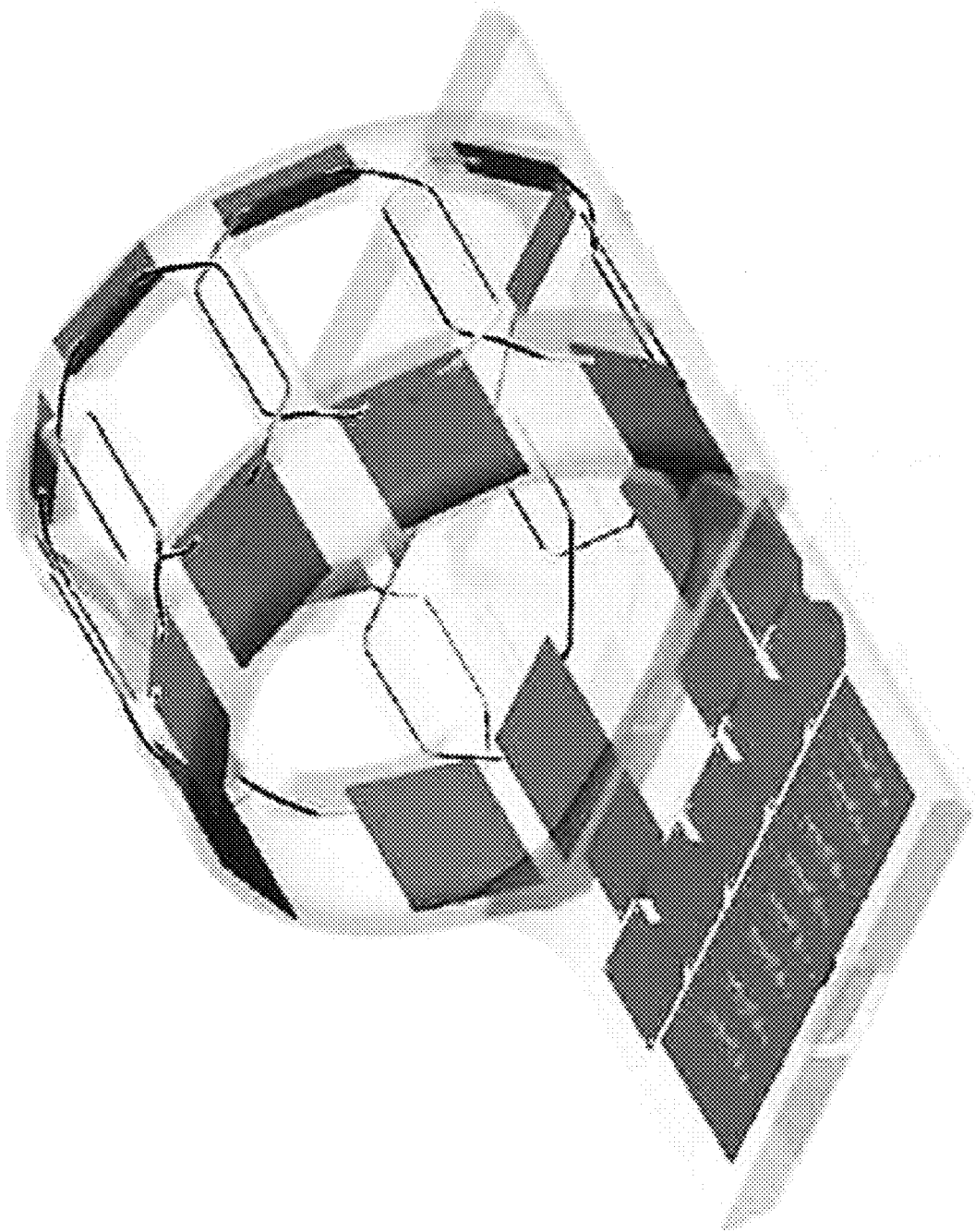

FIG. 4C shows a perspective view of one example of inductive applicator pairs integrated into an applicator system for targeted deep RF radiation-induced hyperthermia.

Figure 5:
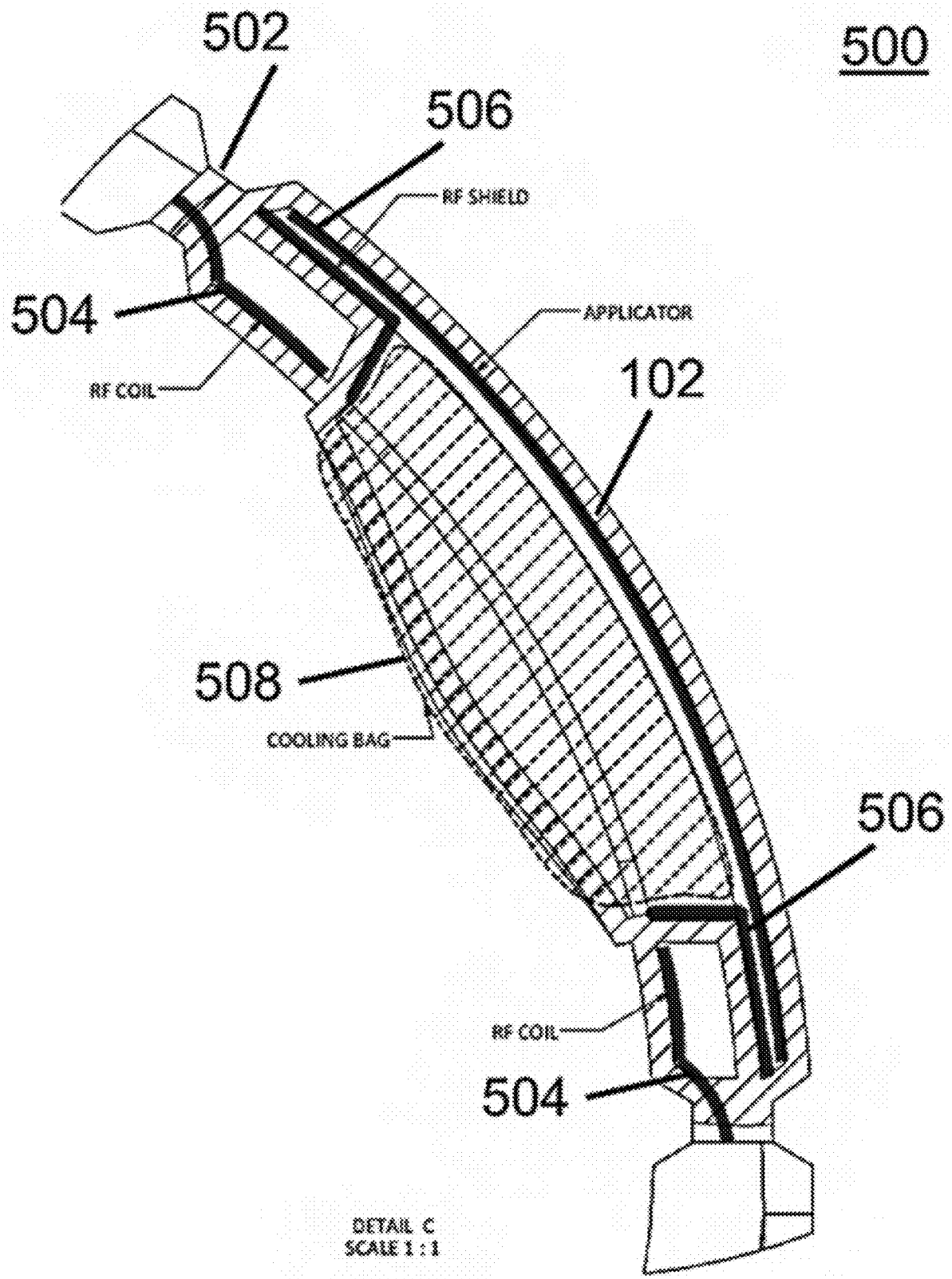

FIG. 5 is a mechanical drawing of an integrated inductive applicator and MR coil for targeted deep RF radiation-induced hyperthermia and thermometry monitoring.

Figure 6B:
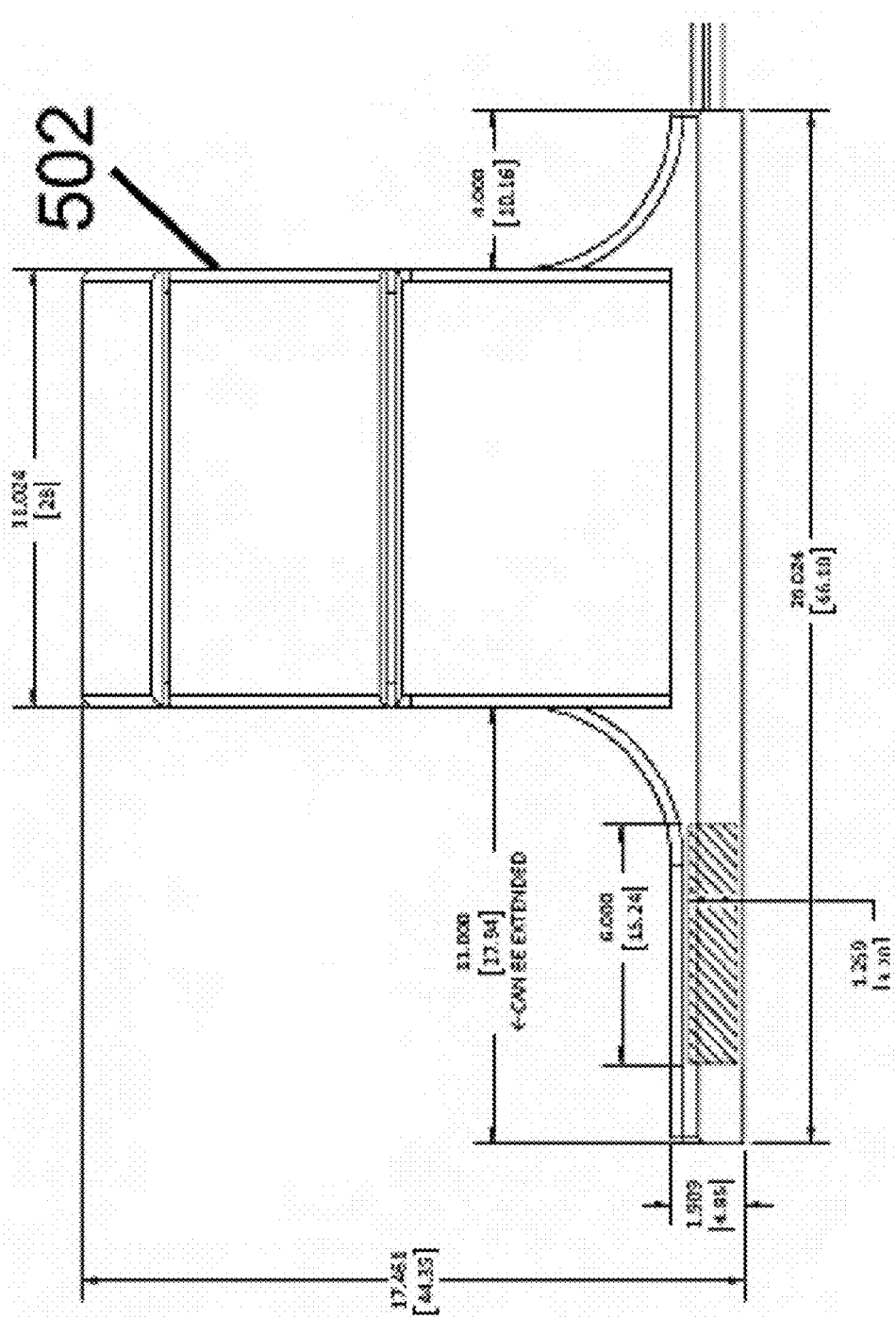

FIG. 6A and FIG. 6B is a mechanical illustration of an integrated applicator system using time-shared inductive applicators for targeted deep RF radiation-induced hyperthermia and MRI coils for real-time thermometry.

Figure 6C:
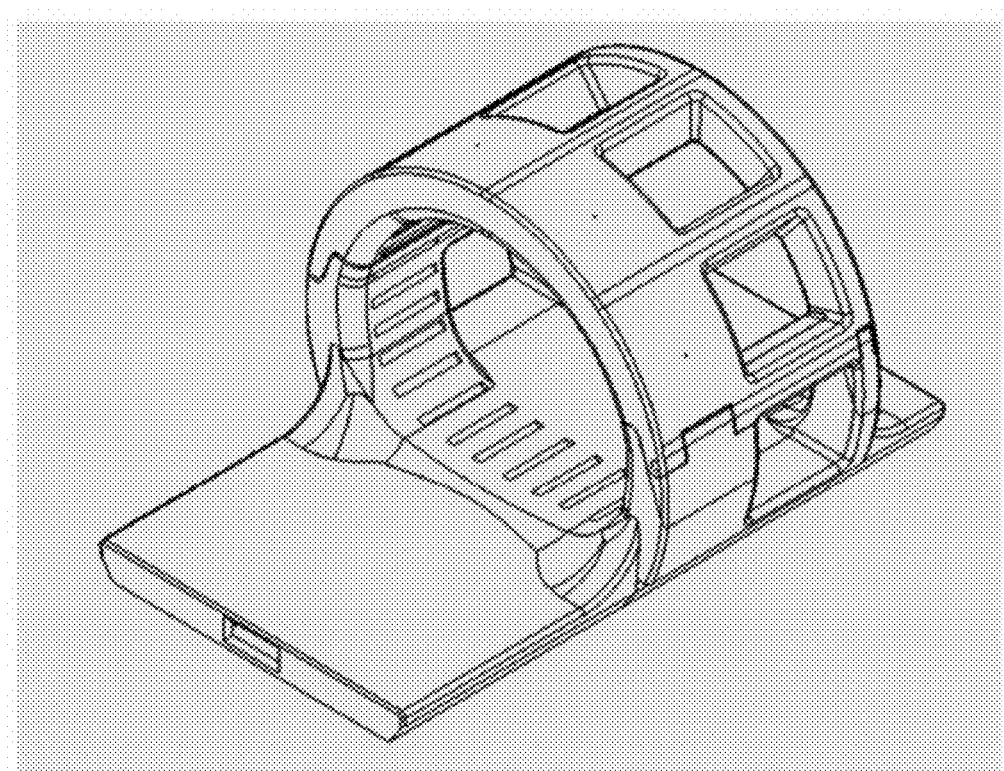

FIG. 6C shows a perspective view of one example of an integrated applicator system using time-shared inductive applicators for targeted deep RF radiation-induced hyperthermia and MRI coils for real-time thermometry.

Figure 6D:
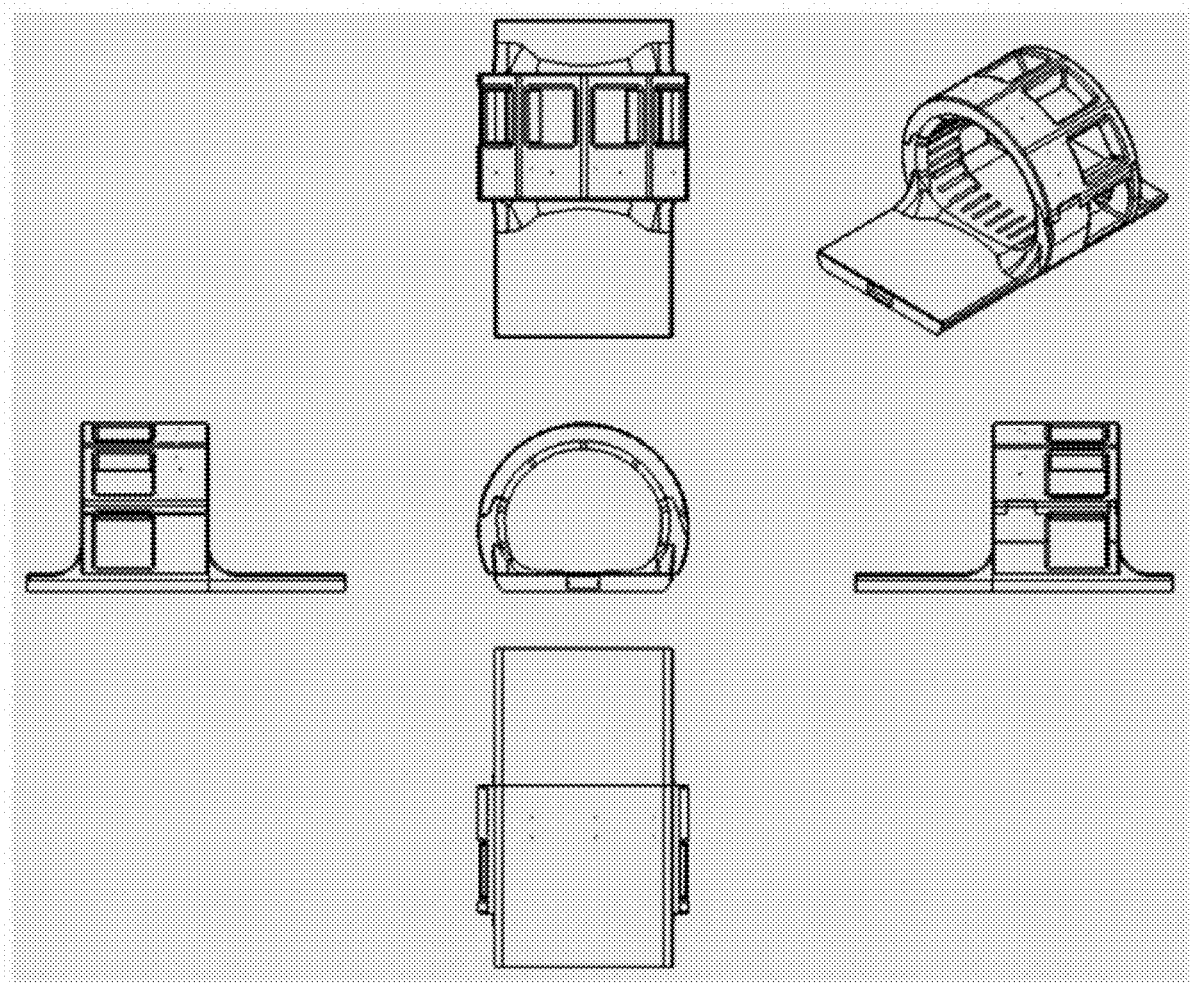

FIG. 6D shows various views (top, bottom, left side, rights side, front, and perspective) one example of an integrated applicator system using time-shared inductive applicators for targeted deep RF radiation-induced hyperthermia and MRI coils for real-time thermometry.

Figure 6E:
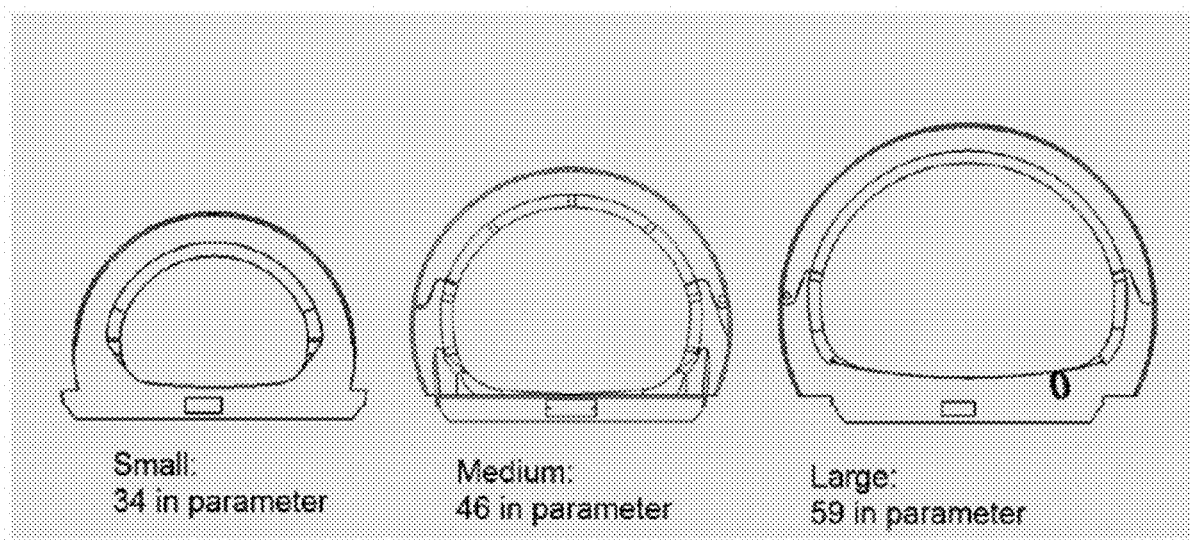

FIG. 6E shows the front view of various sized examples of integrated applicator system using time-shared inductive applicators for targeted deep RF radiation-induced hyperthermia and MRI coils for real-time thermometry.

Figure 6F:
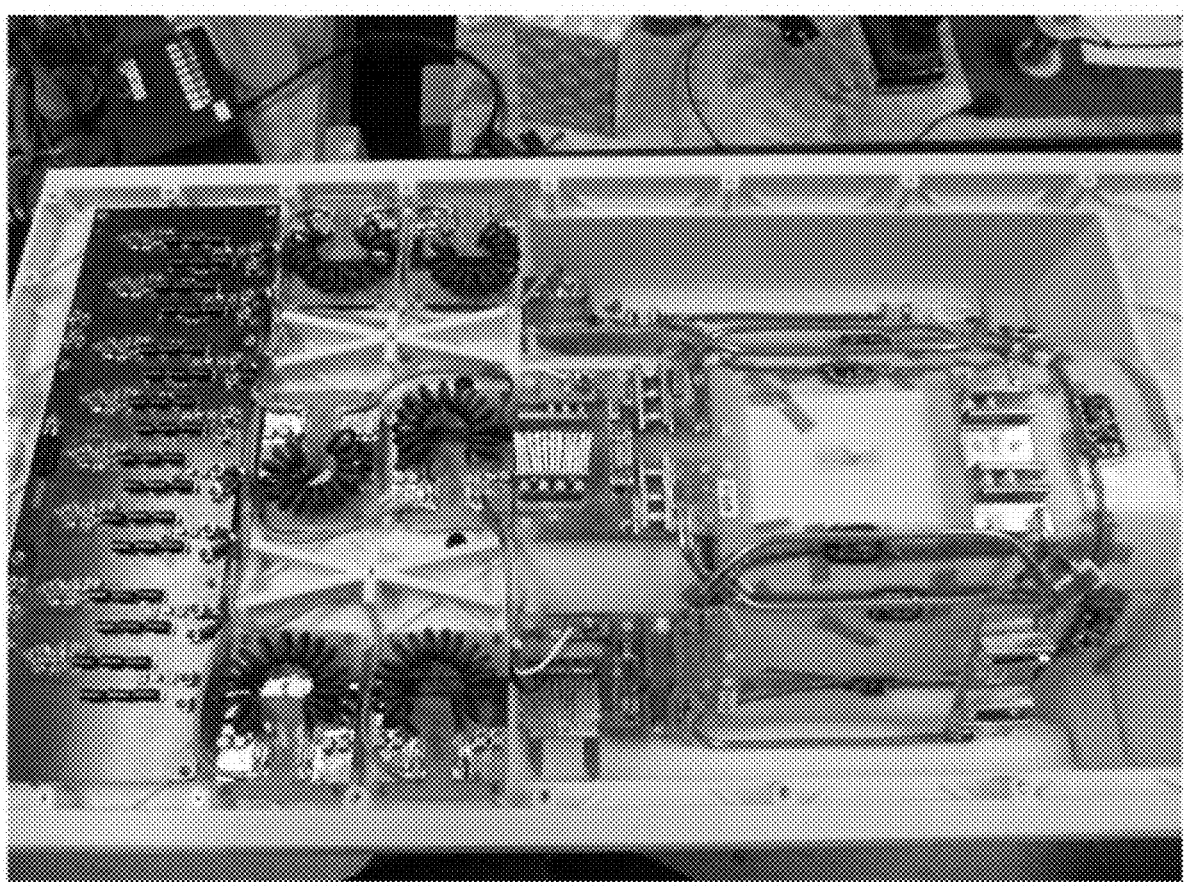

FIG. 6F shows an inductive applicator according to one embodiment of the invention (right) and a solid state switch board that may be integrated into the applicator system (left). The coils shown (right) are 22-24 cm loops, with 3 in the base and one in each section of the top (not all coils are shown). This device was used to obtain animal data, shown in FIGS. 8A and 8B, infra.

Figure 6G:
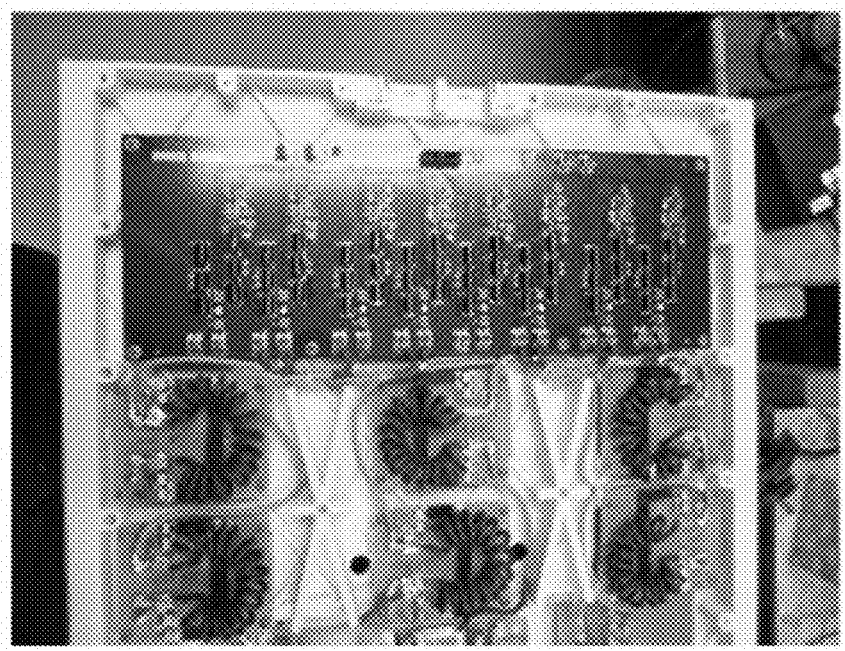

FIG. 6G shows an MRI safe solid-state switch board that may be integrated into the applicator system according to some embodiments of the disclosed invention.

Figure 7:
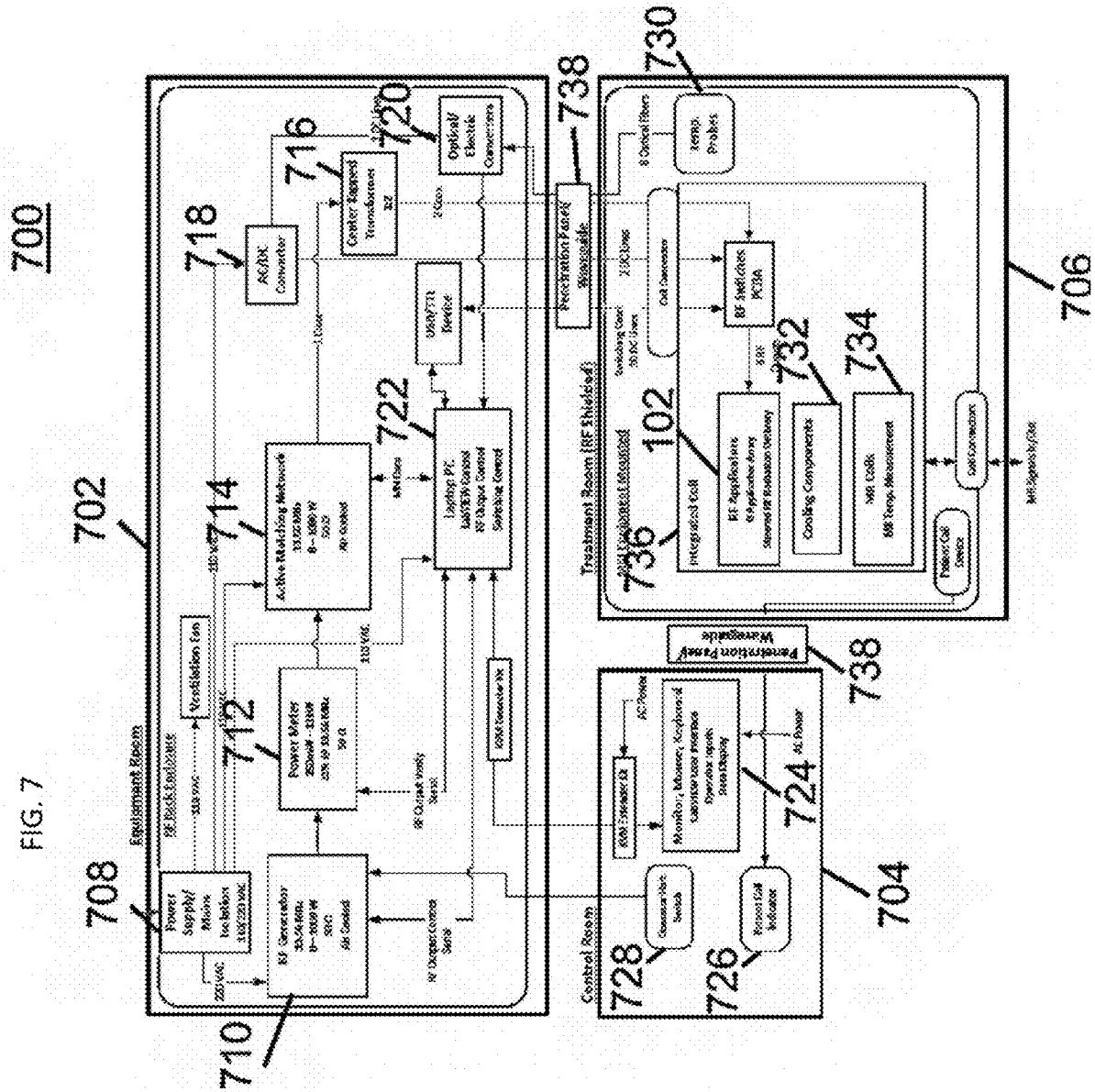

FIG. 7 is an example of an integrated system using timeshared inductive applicators for targeted deep RF radiation-induced hyperthermia.

Figure 8A:
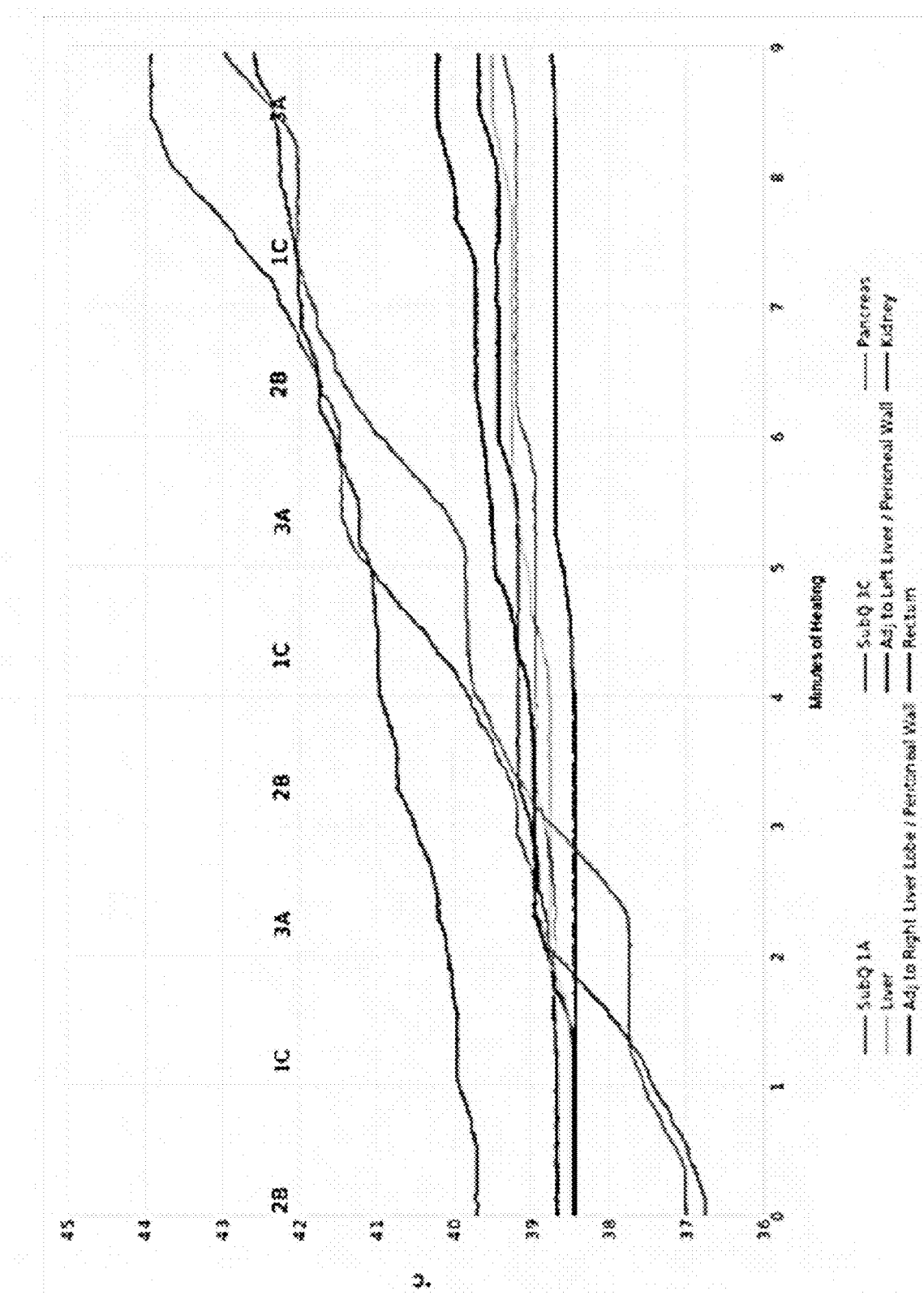

FIG. 8A shows differential heating of tissue resulting from power switching between three different inductive applicator coil pairs (each pair 180° opposites) according to one embodiment of the disclosed invention.

Figure 8B:
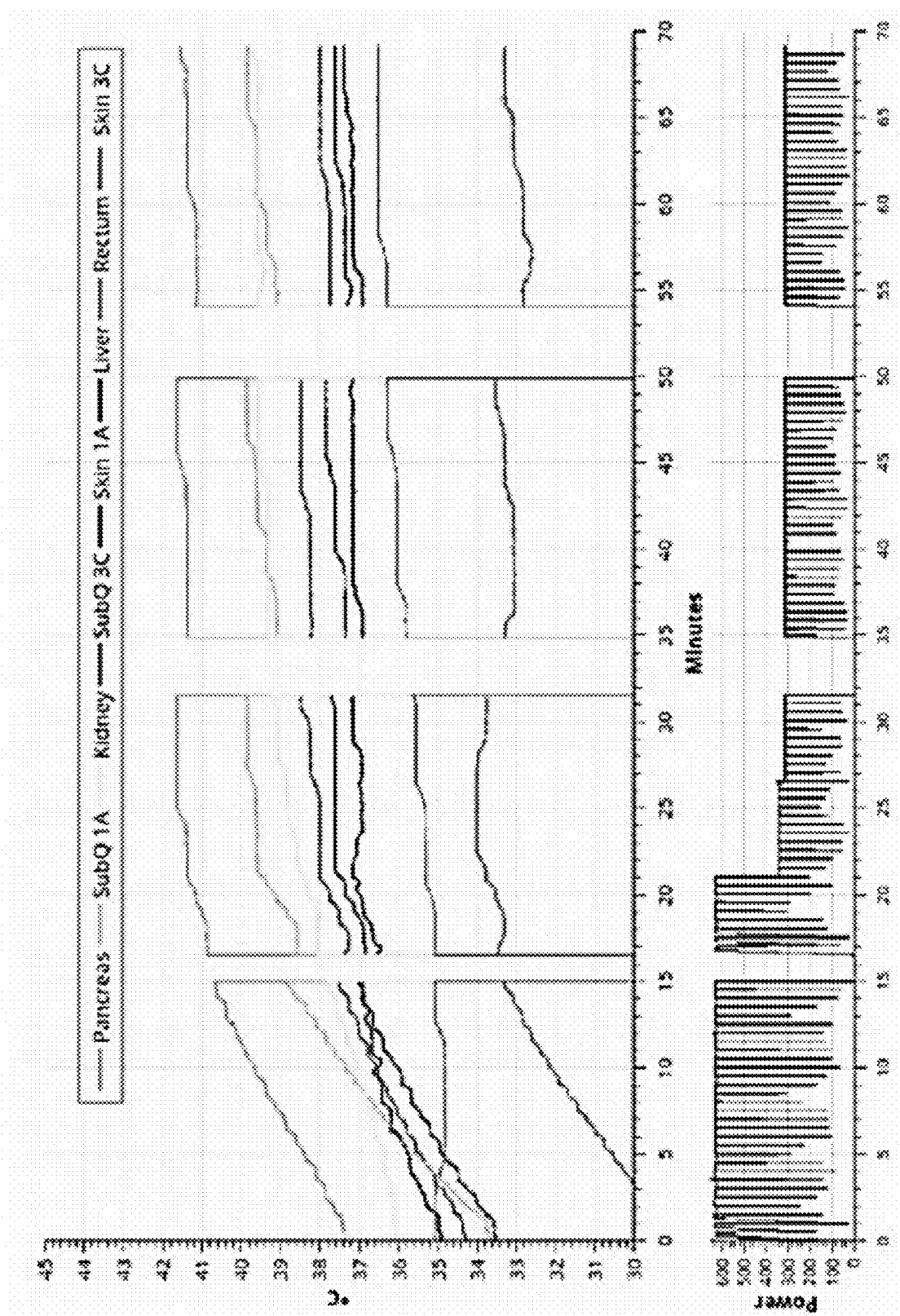

FIG. 8B shows differential heating of tissue resulting from high power ramp up to temperature and low-power hold time of inductive applicators according to one embodiment of the disclosed invention.

Figure 9:
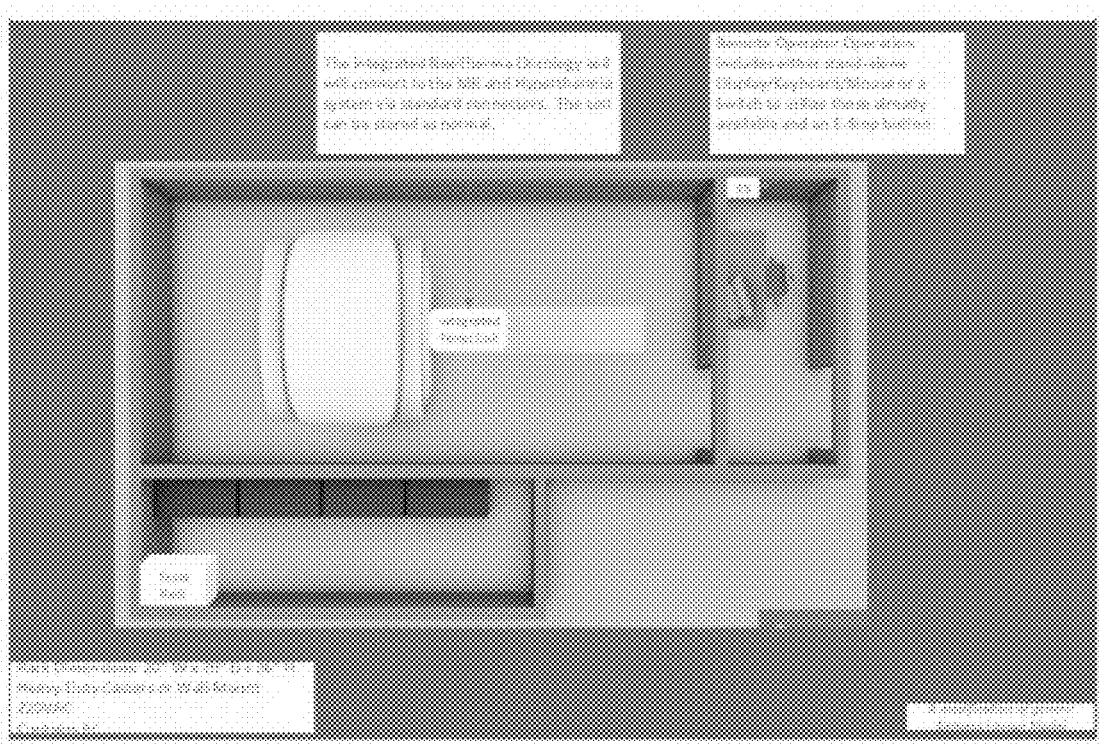

FIG. 9 is a top view of the equipment, control and treatment rooms according to some embodiments.

Figure 10A:
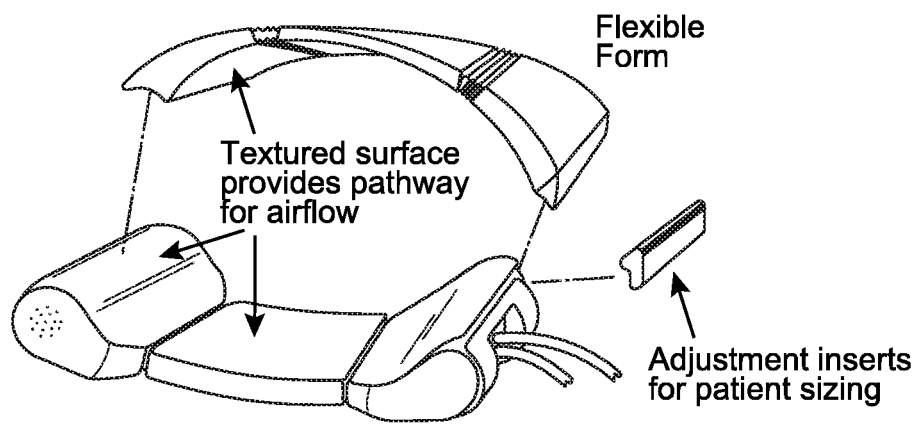
Figure 10B:
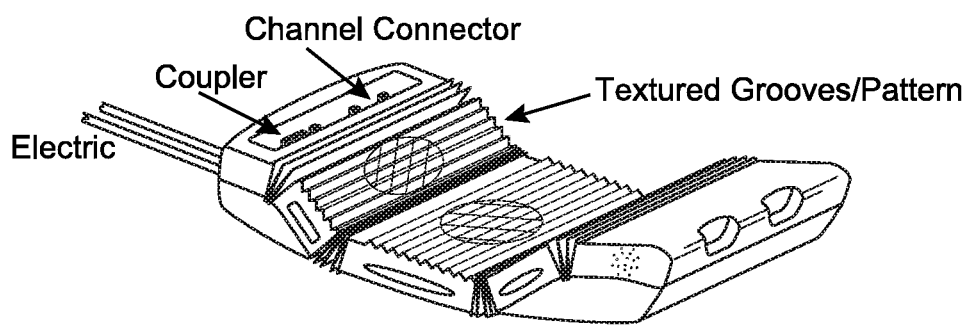
Figure 10C:
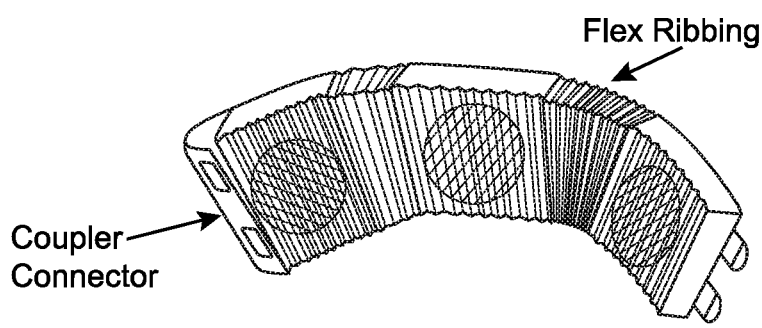

FIG. 10A, FIG. 10B, and FIG. 10C are examples of the flexible articulated links that include the integrated coils according to some embodiments.

DETAILED DESCRIPTION

The disclosed subject matter relates to systems and methods for targeted deep hyperthermia by time-shared RF inductive applicators. Specifically, the RF inductive applicators are capable of providing targeted radiation to selective tissue while minimizing heat exposure to surrounding healthy tissue and also allow for the real-time integration of thermometry monitoring.

Targeted and selective radiation may be accomplished using inductive applicators that utilize hybrid drive and rely on the generation of directly coupled E-fields and coupled magnetic fields which produce induced currents, (e.g. Eddy currents). For example, such hybrid drive allows for the use of local E-fields and coupled E-fields with H-fields generated by pairs of resonant magnetic field loops (e.g., coils). Specifically, the resonant magnetic field loops can be designed as a derivative of Helmholtz pairs ensuring uniformity of the magnetic field in the area between them. Moreover, such inductive applicator pairs allow for both on and off axis targeting by being independently controlled and deactivated when not in use. In addition, such inductive applicators can be integrated with real-time MR thermometry to provide for adjustable and learnable heat patterns that are customized for each patient and/or targeting area in order to provide efficient deep targeting for hyperthermia treatment. Mixtures of different orientation of coils (such as one applicator containing multiple pancake coils which lay relatively normal to the vertical axis of the patient and coils which are circumferential to the vertical axis) may also be used which allow the system to have additional methods by which to target the therapy.

Thus, according to one aspect, the present disclosure provides targeted deep hyperthermia techniques using time-shared RF inductive applicators that can be independently controlled in order to heat desired areas of interest while minimizing heat exposure to surrounding areas and are also integrated with real-time thermometry monitoring.

Such efficient techniques rely on hardware and software components including one or more pairs of RF inductive applicators that can be controlled to provide personalized treatment plans using real-time thermometry monitoring by, for example, integration with a diagnostic device such as a Magnetic Resonance Imagining (MRI) device. Specifically, these RF inductive applicators are driven by one or more RF generators and are formed by opposing resonant magnetic field loops (e.g., coils) that can be independently operated such that they provide both on and off-axis targeted radiation. In addition, such inductive applicators can be of different sizes and can overlap to create more efficient radiation targeting for hyperthermia treatment. Furthermore, the inductive applicators can be integrated with MR coils and used in conjunction with an MRI in order to provide real-time thermometry monitoring thus creating a feedback system whereby the measured temperature can be provided in the form of a heat map in order to adjust one or more parameters of the inductive applicators (e.g., time-switching, power etc.) to ensure efficient and deep targeting of, for example, malignant tissue (e.g., cancer tissue) (See FIG. 1B). Furthermore, such feedback system can be employed on a pre-planned heat map (e.g., one derived from population estimates/models) in order to optimally adjust one or more parameters of the inductive applicators and provide individualized treatment.

In the following description, reference is made to the accompanying drawings that form a part hereof, and in which is shown by way of illustration specific embodiments in which the inventive principles may be practiced. It is to be understood that other embodiments may be utilized and structural changes may be made without departing from the scope of the disclosed subject matter.

Referring now to the drawings in which like numerals represent the same or similar elements, FIG. 1A shows one resonated pair of inductive applicators (not shown, located top and bottom) and a resulting H-field for targeted deep RF radiation-induced hyperthermia. This H-field plot clearly illustrates the potential of deep heating caused by Eddy currents due to the resonating coils. Inductive applicators can be of any size and/or form (e.g., surface coils, circumferential body coils etc.). By utilizing 8 different coils and different configurations of time-sharing, the resulting SAR can contain a hot-spot of and which is centralized (FIG. 1B) or non-centralized (FIG. 1C). Different configurations of coils and time-sharing allotment can be extended to move the hotspot to other locations than depicted in FIG. 1C. A hypothetical rendition of a time-averaged heat map of multiple coil pairs with equal allotments overlaid on an MRI of a human body is shown in FIG. 1E.

FIG. 2 illustrates an E-field plot 200 for two pairs of activated inductive applicators 102. Specifically, plot 200 clearly shows that the generated E-field due to the activation of the opposing inductive applicators is greater in strength surrounding the applicators and thus demonstrates the weakness of a single-pair system, but also allows for targeted deep hyperthermia treatment by time sharing multiple coil pairs. By utilizing multiple applicators similar to the one shown, the time-averaged energy deposition could occur in the center (with equal time allotments) or non-center (with unequal time allotments).

FIG. 3 illustrates an E-field plot 300 for four pairs of activated inductive applicators 102. Specifically, plot 300 clearly shows that the generated E-field due to the activation of all inductive coils results in significant heating in a broad area between the coils and thus allows for broad hyperthermia treatment. In some embodiments, activation of more than one pair of inductive applicators 102 in a specific time-shared manner may be used depending on the needs of the patient (e.g., treatment area, patient heat map etc.).

FIG. 4A shows the time-shared RF inductive applicator for targeted deep RF radiation-induced hyperthermia. Specifically, the inductive applicator is formed by coils 102 that are overlapping. In some embodiments the overlap can be of 90° and/or any other suitable range. Such overlap allows for a larger diameter and thus deeper heating during activation of the pairs.

FIG. 4B shows a single inductive coil for targeted deep RF radiation-induced hyperthermia. Inductive coils 102 can be formed using any suitable conductive material and can have any suitable shape. In some embodiments, inductive coils 102 can be a surface coil and/or a circumferential body coil.

FIG. 4C shows several inductive applications for targeted deep RF radiation-induced hyperthermia arranged circumferentially in an apparatus according to one embodiment of the disclosed invention. The figure also shows the electronic solid-state switches which are MRI safe located in the base of the housing.

FIG. 5 shows a cross-section view of integrated inductive applicator 102 when utilized together with real-time thermometry monitoring with a diagnostic device such as an MRI. Specifically, mechanical housing 502 enclosing one or more hardware components that are capable of delivering RF radiation for targeted heating of a patients region of interest. In some embodiments, mechanical housing 502 can be constructed by articulated links of any suitable material such that it can include overlapping MRI receive coil elements, applicators, bolus bags, drive circuitry, connecting cables and any other hardware component. For example, inductive applicator 102 is separated by RF receive coils 504 through a reflective RF shield 506 so as to hinder any interference of the H-fields and dissipation of power during hyperthermia treatment and temperature monitoring. In some embodiments such housing 502 represents an integrated housing for MRI and hyperthermia treatment. Furthermore, mechanical housing 502 can include cooling bag (e.g., bolus) 508 that ensures that local E-fields that may cause harm to the patient upon contact with the applicator are alleviated.

FIG. 6A shows a frontal view of the integrated mechanical housing 502 including four pairs of inductive coils 102. These pairs are placed in opposing manner so as to resonate in Helmholtz mode and induce deep targeted hyperthermia.

FIG. 6B shows a side view of the integrated mechanical housing 502 including four pairs of inductive coils 102 and the RF receive coils of the MRI used for real-time thermometry monitoring.

FIG. 6C and 6D shows perspective, side, front, top and bottom views of the integrated mechanical housing according to one embodiment, including four pairs of inductive applicators and RF receive coils of the MRI (not shown) for real time thermometry monitoring. FIG. 6E shows a front view of the various sized integrated mechanical housing.

FIG. 6F shows an inductive applicator according to one embodiment of the invention (right) and a solid state switch board that may be integrated into the applicator system (left). The coils shown (right) are 22-24 cm loops, with 3 in the base and one in each section of the top (not all coils are shown). This device was used to obtain animal data, shown in FIGS. 8A and 8B, infra.

FIG. 7 shows a thermometry integrated system 700 using time-shared inductive applicators for targeted deep RF radiation-induced hyperthermia. Integrated system 700 includes equipment room 702, control room 704 and treatment room 706.

Equipment room 702 includes AC power supply 708 that powers one or more RF signal generators 710 that generate RF signals with a frequency of 13.56 MHZ. Power meter 712 measures the power of the signals generated by the one or more RF generators 710 and subsequently the signals are provided to active matching network 714 that provides impedance matching in order to ensure that signal reflection is minimized while power transfer is maximized. A center tapped transformer and/or power divider 716 is used depending on the number of RF generators providing the RF signals to the integrated hyperthermia system located in the treatment room 706. Additionally, an alternating current to direct current (AC/DC) converter 718 is used to power optical and electrical converters 720. Furthermore, active matching network 714 exchanges data with control elements (e.g., RF output, switching etc.) and laptop PC 722 and subsequently provides the data to control room 704.

Control room 704 includes input devices (e.g., mouse, keyboard, monitor etc.) 724 whereby an operator of the hyperthermia system can provide necessary control inputs to the system and review measured data through a user interface. Control room 704 also includes patient call indicator 726 and operation halt switch 728 that terminates operation of system 700.

Treatment room 706 includes temperature probes 730 that can provide temperature measurements to the equipment room in order to control parameters of RF generators 710. In addition, treatment room 706 includes RF inductive applicators 102, cooling components 732 and RF coils 734 used by the MRI machine that are housed in integrated housing 736. Data and signals are exchanged among the equipment room 702, control room 704 and treatment room 706 using penetration panels 738.

It should be noted that the system in FIG. 7 is merely meant to demonstrate an exemplary embodiment of an operating environment and should not be construed as limiting in any manner whatsoever. The particular configuration in FIG. 7 can be altered in numerous ways without departing from the principles herein. For example, RF inductive applicators 102 and RF coils 504 can be housed separately.

The following examples are provided to further illustrate the methods of the present invention. These examples are illustrative only and are not intended to limit the scope of the invention in any way.

EXAMPLE 1

As seen in FIG. 8A, data was obtained showing targeted hyperthermia in a porcine animal model using one embodiment of the apparatus disclosed herein (e.g. FIG. 4A, FIG. 6F, FIG. 6G). Power was delivered at 600 W to a 90 pound porcine specimen with surgically implanted fiber optic temperature probes. Three inductive applicator coil pairs (labeled 2B, 1C, and 3A) were separated by about 60° around the circumference of the apparatus (and circumferential to the porcine subject), with each pair 180° from one another. 2B is the top center and bottom center, 1C is the top left (when viewed from the bottom) and bottom right. (See FIG. 6F, which depicts coils bottom center (coil B), bottom right (coil C), and bottom left (coil A); top coils 1, 2 and 3 are not shown). The power was switched between the three different coil pairs in 60 second intervals. Fiber optic temperature probes where located in subcutaneous fat (SubQ) between the left coils (SubQ1A) and right coils (SubQ3C), as well as in the liver, pancreas, kidney, adjacent to the left liver lobe/peritoneal wall, adjacent to the right liver lobe/peritoneal wall, and rectum.

As shown in the graph of FIG. 8A, different coil pairs result in heating different areas of the subject over a 9 minute ramp up. For example, the subject's kidney responds to coil configurations 2B and 3A, but not 1C. This is evident by the temperature rises of the kidney temperature probe during the one minute intervals when coil pair 2B and 3A are powered, but minimal temperature rises when coil pair 1C is powered. By contrast, other organs, such as the liver and pancreas, have notably lesser increases in temperature during the specific cycling of the coil pairs, and they responded to other pairs (pancreas increases most readily with pair 3A). Thus, without being limited by theory, the location of the kidney relative to the time-averaged hotspot of the coil pairs and/or the electrical properties of the kidney (e.g. high permittivity, good conductivity) enabled the kidney to heat up the most, followed by the pancreas and the liver, in this particular embodiment.

EXAMPLE 2

As seen in FIG. 8B, data was also obtained showing targeted hyperthermia in a porcine animal model over a temperature ramp up followed by maintenance of elevated temperature for a total time of 70 minutes using one embodiment of the apparatus disclosed herein (e.g. FIG. 4A, FIG. 6F, FIG. 6G). In this example, power was initially delivered at 600 W during ramp up until the pancreas temperature probe (green line) reach 39.5° C. (about 7 minutes). Power was cycled between the coil pairs (as described above) in 30 second intervals (see brief power drops about every 30 seconds indicating switching). All temperature probes were monitored and power was reduced once the temperature of the pancreas probe had reached a target temperature within the 39.5° C.-43° C. range, while avoiding increased temperature in other locations (i.e. over 44° C.). In this example, power was manually reduced when the temperature of the pancreas probe reached 41° C. (around 21 minutes) and a "maintenance" power of 300 W was applied for approximately one hour resulting in a stable temperature reading of about 41.5° C. by the pancreas probe. Power could further be reduced or increased while aiming to keep the pancreas temperature constant. In this example, the readings and power were paused each 15 minutes to observe the porcine subject's vital signs. Temperature probes were placed in a 125 pound porcine specimen located in the pancreas, left and right side subcutaneous fat ~1 cm deep (SubQ), kidney, liver, rectum, and directly on the surface of the skin with a small amount of gel for thermal transfer.

As seen in the graph of FIG. 8B, the targeted hyperthermia resulted in maintenance of organ specific temperature differences for a sustained period of time. The pancreas was held at the highest temperature, followed by kidney, liver, and rectum.

The embodiments described in this disclosure can be combined in various ways. Any aspect or feature that is described for one embodiment can be incorporated into any other embodiment mentioned in this disclosure. Moreover, any of the embodiments described herein may be hardware based, software-based and/or comprise a mixture of both hardware and software elements. Accordingly, while various novel features of the inventive principles have been shown, described and pointed out as applied to particular embodiments thereof, it should be understood that various omissions and substitutions and changes in the form and details of the systems and methods described and illustrated, may be made by those skilled in the art without departing from the spirit of the invention. Amongst other things, the steps of any described methods may be carried out in different orders in many cases where such may be appropriate. Those skilled in the art will recognize, based on the above disclosure and an understanding therefrom of the teachings of the inventive principles, that the particular hardware and devices that are part of the system described herein, and the general functionality provided by and incorporated therein, may vary in different embodiments of the inventive principles. Accordingly, the particular system components are for illustrative purposes to facilitate a full and complete understanding and appreciation of the various aspects and functionality of particular embodiments of the present principles as realized in system and method embodiments thereof. Those skilled in the art will appreciate that the inventive principles can be practiced in other than the described embodiments, which are presented for purposes of illustration and not limitation.

What is claimed is:

1. A system for targeted hyperthermia, the system comprising:
one or more radio frequency (RF) generators; one or more pairs of inductive applicators coupled to the one or more RF generators and configured to deposit radio frequency radiation on a region of interest based on a set of configurable parameters, wherein the one or more pairs of inductive applicators further comprise one or more semi-planar inductive loops that are configured to be temporally switched to provide targeted heating; a temperature measuring device coupled to the one or more pairs of inductive applicators; and a hardware processor configured to receive temperature measurements from the temperature measuring device and cause a change on the set of configurable parameters of the one or more pairs of inductive applicators based on the received temperature measurements.

2. The system of claim 1, wherein the one or more pairs of inductive applicators utilize a hybrid drive by employing a local direct E-field and an E-field coupled to an H-field.

3. The system of claim 1, wherein the one or more pairs of inductive applicators operate in Helmholtz mode and are oriented in opposite sides causing H-field coupling and deep-seated E-field penetration.

4. The system of claim 1, wherein the one or more pairs of inductive applicators further comprise one or more semi-planar inductive loops that are configured to be temporally switched to minimize superficial heating outside the region of interest.

5. The system of claim 1, wherein the one or more pairs of inductive applicators further comprise one or more semi-planar inductive loops that are configured to be temporally switched to enhance targeted heating.

6. The system of claim 1, wherein the one or more pairs of inductive applicators further comprise one or more semi-planar inductive loops and are configured to overlap so as to increase the diameter of the one or more semi-planar inductive loops.

7. The system of claim 1, wherein the one or more pairs of inductive applicators further comprise one or more semi-planar inductive loops of different sizes.

8. The system of claim 1, wherein the one or more pairs of inductive applicators are operated using two RF generators operating 180° out of phase with each other via circuitry and the one or more pairs of inductive applicators are selectable by electronic switches.

9. The system of claim 1, wherein the set of configurable parameters for the one or more inductive applicators include amplitude modulation, electronic switching, and time in order to modify the targeted treatment zone.

10. The system of claim 1 further comprising a mechanical housing enveloping the one or more pairs of inductive applicators and an integrated MR coil included in the temperature measuring device.

11. The system of claim 1, wherein the temperature measuring device is a Magnetic Resonance Imaging (MRI) device.

12. The system of claim 11 further comprising magnetic resonance (MR) compatible solid-state switches that switch at the point of the one or more inductive applicators in order to minimize cable matching issues.

13. The system of claim 11 further comprising magnetic resonance (MR) compatible solid-state switches that switch inside a magnet room in order to minimize a number of cables needed to pass through a penetration panel.

14. The system of claim 11, wherein the one or more pairs of inductive applicators and a set of MR coils of the MRI device are transparent to each other by geometric and tuned blocking circuitry.

15. The system of claim 14, wherein geometric and tuned blocking circuitry include reflective floating shields.

16. The system of claim 1, wherein operation of the one or more inductive applicators is terminated based on use of the one or more pairs of inductive applicators.

17. The system of claim 1, wherein the hardware processor is configured to automatically extract and update pre-planned heat deposition patterns using real-time MR feedback.

18. The system of claim 17, wherein the pre-planned heat deposition patterns are obtained using population estimates.

19. The system of claim 17, wherein the hardware processor is configured to generate a temporally-adjusted plan for the one or more pairs of inductive applicator and power for the remainder of treatment with MR feedback.

20. The system of claim 1, wherein the one or more pairs of inductive applicators are oriented in non-opposing locations with moderate coupling in order to direct energy off-axis.

21. The system of claim 1 further comprising one or more flexible articulated links enclosing the one or more pairs of inductive applicators such to ensure consistent contact with the patient in order to limit the required tuning range and patient comfort.

22. The system of claim 21, wherein the one or more flexible articulated links overlap creating a wide variety of patient sizes that can be accommodated with a single coil.

23. The system of claim 1, wherein the one or more pairs of inductive applicators further comprise at least six semi-planer inductive loops equally spaced circumferentially around the patient and configured to be temporally switched to provide targeted heating or minimize superficial heating outside the region of interest.

24. The system of claim 1, wherein the system is effective to heat at least one of the patient's organs to a temperature that is at least 0.5° C. greater than the temperature of another of the patient's organs.

25. The system of claim 1, wherein the system is effective to maintain a temperature differential of at least 0.5° C. between two or more of the patient's organs for at least 40 minutes.

26. The system of claim 23, wherein at least one pair of inductive applicators is effective to differentially heat at least one organ in the patient relative to another organ.

27. The system of claim 23, wherein at least one pair of inductive applicators is effective to differentially heat at least one internal organ relative to another internal organ of the patient.

28. The system of claim 23, wherein the system is effective to differentially heat the patient's kidney relative to at least one other internal organ.

29. The system of claim 23, wherein the system is effective to differentially heat the patient's pancreas relative to at least one other internal organ.

30. The system of claim 23, wherein the system is effective to differentially maintain the temperature of the patient's kidney at least 0.5° C. above the temperature of at least one other internal organ.

31. The system of claim 23, wherein the system is effective to differentially maintain the temperature of the patient's pancreas at least 0.5° C. above the temperature of at least one other internal organ.

32. The system of claim 1, wherein the one or more RF generators are used and the selection of their phase angle is made by use of electronic switching.

* * * * *